United States Patent [19]
Watson

[11] 3,988,212
[45] Oct. 26, 1976

[54] POLYMERIZATION INHIBITOR FOR VINYL AROMATIC COMPOUNDS

[75] Inventor: James M. Watson, Big Spring, Tex.

[73] Assignee: Cosden Technology, Inc., Big Spring, Tex.

[22] Filed: Mar. 21, 1975

[21] Appl. No.: 560,349

[52] U.S. Cl. .................................. 203/9; 203/59; 203/65; 260/669 A
[51] Int. Cl.$^2$ .......................................... B01D 3/34
[58] Field of Search ............... 203/9, 8, 58, 65, 59; 260/669 A

[56] References Cited
UNITED STATES PATENTS

| | | | |
|---|---|---|---|
| 2,556,030 | 6/1951 | Coulter et al. | 203/9 |
| 3,816,265 | 6/1974 | Daniels et al. | 203/9 |

OTHER PUBLICATIONS

Bundy et al: Styrene, Its Polymers, Copolymers and Derivatives, (1952) pp. 1236, 1237, 1238.
Foord, *J. Chem. Soc.* pp. 48–56 (1940).

*Primary Examiner*—Wilbur L. Bascomb, Jr.

[57] ABSTRACT

Disclosed is a process for the distillation of readily polymerizable vinyl aromatic compounds and a new polymerization inhibitor therefor. The process comprises subjecting a vinyl aromatic compound to distillation conditions in a distillation system and adding to the system the new polymerization inhibitor comprising a mixture of N-nitroso diphenyl amine and a dinitro-O-cresol.

12 Claims, No Drawings

POLYMERIZATION INHIBITOR FOR VINYL AROMATIC COMPOUNDS

BACKGROUND OF THE INVENTION

The present invention relates to a process for the distillation of readily polymerizable vinyl aromatic compounds. More particularly, the present invention relates to a process for the vacuum distillation of styrene, substituted styrene, divinylbenzene and polyvinylbenzenes wherein the amount of said materials polymerized during distillation is reduced over an extended period of time.

it is well known that vinyl aromatic compounds such as monomeric styrene, lower alkylated styrene, e.g., alpha-methyl styrene, and divinylbenzene polymerize readily, and furthermore, that the rate of polymerization increases with increasing temperature. Inasmuch as styrene and divinylbenzene produced by common industrial methods contain impurities, these compounds must be subjected to separation and purification processes in order to be suitable for most types of further industrial use. Such separation and purification is generally accomplished by distillation.

In order to prevent polymerization during distillation of vinyl aromatic compounds, various types of known polymerization inhibitors have been employed in connection with prior art distillation processes. For example, common inhibitors useful for inhibiting the polymerization of vinyl aromatics under distillation conditions include 4-tert-butylcatechol (TBC) and hydroquinone. It is preferred, however, to purity vinyl aromatics by using vacuum distillation techniques, whereby these commonly employed inhibitors are rendered unsuitable in view of the fact that they are effective only in the presence of oxygen. The partial pressure of oxygen in a vacuum distillation column is accordingly too low for these conventional inhibitors to be effective. Sulphur is perhaps the polymerization inhibitor most commonly employed to inhibit polymerization of vinyl aromatic compounds during distillation, since sulphur does provide effective inhibition in the absence of oxygen. While sulphur provides a reasonably effective inhibitor, its use in distillation processes results in one very significant disadvantage, namely, there is formed in the reboiler bottoms of the distillation column a valueless waste material which is highly contaminated with sulphur. This waste material furthermore represents a significant pollution or waste removal problem.

Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any utility for inhibiting vinyl aromatic polymerization under distillation conditions, particularly under vacuum distillation conditions. In addition, certain compounds which are useful for inhibiting polymerization of one type of vinyl aromatic compound, for example, styrene, have proved to be essentially ineffective for inhibiting polymerization of another species of vinyl aromatic compound, for example, divinylbenzene. A limited number of nitroso compounds have proven to be effective for inhibiting polymerization of styrene monomer during distillation. For example, N-Nitroso phenylhydroxylamine and p-nitroso-N,N-dimethylaniline are reasonable effective inhibitors for the distillation of styrene, although they are not particularly soluble in styrene monomer. On the other hand, N-nitroso diphenylamine disclosed in U.S. Pat. No. 3,816,265, assigned to the assignee of the present application has been demonstrated to be a particularly effective polymerization inhibitor under vacuum distillation conditions for both styrene and divinylbenzene, whereas, N,N-nitroso-methylaniline as disclosed in U.S. patent application Ser. No. 288,138, also assigned to the assignee of the present application, has been found to be an excellent polymerization inhibitor for styrene under vacuum distillation conditions. One of the most effective inhibitor systems known for divinylbenzene comprises a mixture of sulphur and N-nitroso phenylhydroxylamine.

In a typical distillation process for vinyl aromatic compounds utilizing a polymerization inhibitor, the mixture of vinyl aromatic to be distilled is generally contacted with the chemical polymerization inhibitor prior to being subjected to distillation conditions in the distillation apparatus. It remains as a significant problem today that the amount of polymer formed in the distillation apparatus and in the high purity product recovered therefrom is substantially higher than desired, and occasionally, that complete polymerization occurs inside of the distillation apparatus. For example, in the process of distilling crude divinylbenzene (a mixture containing divinylbenzenes, diethylbenzenes and monovinylbenzenes) to obtain high purity divinylbenzenes, even when inhibited with sulphur and TBC, a divinylbenzene product is obtained which contains significant quantities of polymer which are difficult to separate from the product and detrimental to the end use of such divinylbenzenes. Furthermore, the material which is removed from the bottom or reboiler area of the distillation apparatus is a highly polluting sulphur-containing waste material which must be disposed of.

It is therefore desirable to provide new polymerization inhibitors which are useful for styrene and vinyl benzenes under distillation conditions, particularly vacuum distillation conditions, and which are not subject to the disadvantages outlined above.

It is therefore an object of the present invention to provide a new and improved process for the distillation of readily polymerizable vinyl aromatic compounds.

A further object of the invention is to provide a new and improved process for the distillation of readily polymerizable vinyl aromatic compounds, which process results in higher recovery of a high purity unsaturated vinyl aromatic compound and concomitantly in the production of less undesirable by-products.

A further object of the invention resides in the provision of a new and improved process for the distillation of vinyl aromatic compounds which results in the production of substantially less polymerized material in the distillation apparatus.

Yet another object of the invention resides in the provision of a new and improved process for the distillation of vinyl aromatic compounds which avoids the production of a highly polluting, contaminated bottom or reboiler residue.

It is also an object of the present invention to provide a new and improved process for the distillation of vinyl aromatic compounds which permits the distillation apparatus to be operated at an increased rate of throughput without a reduction in efficiency.

It is still a further object of the present invention to provide a new and improved process for the distillation of vinyl aromatic compounds which provides all of the foregoing enumerated advantages in a vacuum distillation process.

A specific object of the invention resides in the provision of a new and improved polymerization inhibitor system for use in the distillation of vinyl aromatic compounds.

SUMMARY OF THE INVENTION

In accomplishing the foregoing and other objects, there has been provided in accordance with the present invention a process for the distillation of a readily polymerizable vinyl aromatic compound comprising subjecting the vinyl aromatic compound to distillation conditions in a distillation system in the presence of an inhibitor system which is a mixture of N-nitroso diphenyl amine (NDPA) and a dinitro-o-cresol (DNOC).

In one aspect of the process according to the invention, the NDPA-DNOC inhibitor mixture is simply introduced into the distillation system by adding it to the reboiler area of the distillation apparatus, or alternatively, by incorporating it into the incoming stream of vinyl aromatic compound to be purified. The amount of the inhibitor mixture necessary to effectively inhibit polymerization of the vinyl aromatic compounds may vary over a wide range depending upon various factors of the distillation process, e.g., temperature, reflux ratio, pressure, residence time, etc. Typically, however, it has been found that an amount of the inhibitor mixture between about 50 and about 3000 ppm is sufficient to inhibit polymerization of vinyl aromatic compounds under normal distillation conditions (105° C,).

Through the use of the process according to the present invention, the amount of polymerization occurring within the distillation apparatus is significantly reduced in comparison to conventionally employed methods. In addition, the amount of desired distillation product is increased in proportion to the decrease in the amount of polymer formation. Still further, the material accumulating in the bottom or reboiler area of the distillation apparatus can be reused, e.g., for its fuel value or for reprocessing, which is a distinct advantage over conventional methods utilizing sulphur as a polymerization inhibitor which produce a highly polluting waste material in the reboiler area. In addition, the present inhibitor mixture is found to produce a synergistic effect when compared to the inhibiting activity of either of the components alone.

Other objects, features and advantages of the invention will become apparent from the detailed description of preferred embodiments which follows:

DESCRIPTION OF THE PREFERRED EMBODIMENTS

The distillation process of the present invention employs an inhibitor system made up of a mixture of N-nitroso diphenyl amine and a dinitro-o-cresol as the polymerization inhibitor during the distillation of vinyl aromatic compounds. Typically, the distillation process is carried out under reduced pressure, e.g., vacuum distillation, and one of the significant advantages of the invention is that the use of sulphur in the distillation system can be avoided.

The mixture of NDPA and DNOC employed as the inhibitor system of the present invention generally contains 10 to 90% by weight of NDPA with the remainder being DNOC. Preferably, however, the amount of NDPA will be within the range of 40 to 60% with the remainder being DNOC. The DNOC's used are the 4,6-dinitro-o-cresol and 3,5-dinitro-o-cresol. The preferred DNOC is the 4,6-dinitro-o-cresol.

The distillation technique of the process of the present invention is suitable for use in virtually any type of separation of a readily polymerizable vinyl aromatic compound from a mixture wherein the vinyl aromatic compound is subjected to temperatures above room temperature. Surprisingly, the process of the present invention has been found particularly useful in vacuum distillation techniques, the preferred method for separating unstable organic liquid mixtures. In its most useful application, the distillation process of the invention is applied to a distillation mixture containing one of the vinyl aromatic compounds selected from the group consisting of styrene, alpha-methylstyrene, vinyltoluene, vinylnaphthalene, divinylbenzenes and polyvinylbenzenes. The preferred application of the present invention relates to the distillation of crude divinylbenzene or crude styrene under vacuum distillation conditions.

The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 50 ppm and about 3000 ppm by weight have generally provided suitable results, depending primarily upon the temperature of the distillation mixture and the degree of inhibition desired. More often, however, with the inhibitor system of the present invention, the NDPA-DNOC mixture is used in concentrations of 100 to 1000 ppm.

During vacuum distillation of the divinylbenzene-containing mixtures and styrene-containing mixtures, the temperature of the reboiler is preferably maintained from about 150° F. to about 250° F. by controlling reboiler pressure at from about 30 mm. to about 400 mm. of Hg. Under such conditions, in a distillation apparatus having a distillation zone containing from about 50 to about 100 distillation stages, inhibitor mixture concentrations of from about 100 ppm to about 2000 ppm by weight are suitable, whereas concentrations of from about 100 ppm to about 600 ppm by weight and preferably, 200 to 600 ppm by weight, in the case of styrene distillation and concentrations in the range of from about 200 ppm to about 1000 ppm by weight are preferred for distillation of divinylbenzene. The foregoing ranges are based upon distillation temperatures of from about 150° to 250° F. and residence times of between about 2 and 4 hours. Obviously, in the lower portions of the temperature and residence time ranges, smaller amounts of inhibitor may be utilized. Obviously, amounts of inhibitor greater than those specified hereinabove may be employed, although the advantages of adding the additional inhibitor are not significant and are outweighed by the corresponding increase in cost.

The polymerization inhibitor of the present invention may be introduced into the distillation apparatus in any convenient manner which permits efficient distribution of the inhibitor throughout the apparatus. Typically and most advantageously, the required amount of inhibitor is simply added to the reboiler area of the distillation column, although equivalent results may be obtained by incorporating the inhibitor into the incoming hot stream of vinyl aromatic compound.

Since the inhibitor is gradually depleted during distillation, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. The means by which the maintenance of the necessary concentration of the inhibitor system is carried out is of no particular importance as long as the concentration of inhibitor is kept about the minimum required level.

Another factor enabling the distillation apparatus to operate at an increased rate in accordance with the present invention as opposed to conventional prior art processes is the fact that the inhibitor system of the present invention is a more efficient inhibitor at normal temperatures than the conventional inhibitors, and will thus permit higher distillation temperatures and higher pressures. In this way, the rate of distillation can be increased without increasing the amount of polymerization which has been deemed to be acceptable in accordance with conventional distillation procedures.

When the process of the present invention is utilized, the bottoms material which accumulates during the distillation process can be drawn off and utilized for its heating value or for reprocessing. This represents another significant advantage in comparison to conventional processes for vacuum distillation of vinyl aromatic compounds which employ sulphur as the polymerization inhibitor, or sulphur in combination with other chemical polymerization inhibitors. In these conventional processes, a bottoms material is formed which is valueless for further use and constitutes a high polluting waste material which must be disposed of and which, in this regard, also presents a problem of disposal.

Upon recovery of the distillation product obtained from the process of the present invention, it is found that a higher percentage of the pure readily polymerizable vinyl aromatic compound is recovered in an unpolymerized state. Moreover, the concentrated distillation residues are more easily handled and removed from the apparatus, as by pumping or the like.

In order to more fully describe the present invention, the following examples are presented which are intended to be merely illustrative and not in any sense limitative of the invention.

EXAMPLE 1

A series of experimental runs were carried out to demonstrate the effectiveness of the present inhibitor system. In these runs, styrene was used as the vinyl aromatic compound. In each run the same amount of styrene was used and the inhibitor containing styrene system was refluxed at 115° C plus or minus 2° C under either an atmosphere of nitrogen or air. The time period for each run was four hours. The inhibitor used, the concentration thereof, the atmosphere under which the run was made and the percent polymer formed is set forth in the following table.

| Run | Inhibitor | Inhibitor Concentration, ppm | Atmosphere | % Polymer |
|---|---|---|---|---|
| 1 | NDPA | 400 | N$_2$ | 12.9 |

-continued

| Run | Inhibitor | Inhibitor Concentration, ppm | Atmosphere | % Polymer |
|---|---|---|---|---|
| 2 | 4,6-DNOC | 400 | Air | 1.9 |
| 3 | 4,6-DNOC | 400 | N$_2$ | 2.5 |
| 4 | 4,6-DNOC | 200 | Air | 14.4 |
| 5 | NDPA+4,6-DNOC | 200+200 | N$_2$ | 1.4 |
| 6 | NDPA+4,6-DNOC | 100+100 | N$_2$ | 5.4 |

The efficacy of the present invention is believed clearly demonstrated by comparison of Runs 1 and 3 with Runs 5 and 6. In Run 1 with 400 ppm of NDPA, 12.9% polymer was obtained, whereas with Runs 5 and 6, 1.4% and 5.4% polymer, respectively, was obtained. This represents an 89% and 58%, respectively, reduction in polymer make. In Run 3, 2.5% polymer was obtained, whereas in comparable Run 5, 1.4% polymer was obtained. This represents a 44% reduction in polymer make.

EXAMPLE 2

The conditions of the experimental runs 1, 3 and 5 of Example 6 are repeated in three runs with the exception that styrene is replaced with divinylbenzene and the amount of inhibitor was increased in each run to 500 ppm. Again, the inhibitor mixture is 50:50 NDPA and 4,6-DNOC. Polymer reduction results similar to those of Run 5 of Example 1 are again obtained.

EXAMPLE 3

Example 2 is substantially repeated with the exception that 3,5-DNOC is used instead of 4,6-DNOC. Styrene is used as the vinyl aromatic compound and the concentration of inhibitor is again reduced to 400 ppm. Again, polymer reduction results similar to those of Run 5 of Example 1 are obtained.

EXAMPLE 4

Example 3 is substantially repeated in four runs with 4,6-DNOC instead of 3,5-DNOC and with the inhibitor mixture used in two of the runs. The NDPA concentrations in one of the mixtures is 40% and in the other 60% by weight of the mixture. Again, polymer reduction is substantially enhanced by use of the inhibitor mixture of the present invention.

What is claimed is:

1. A process for the distillation of a readily polymerizable vinyl aromatic compound, which comprises subjecting said compound to distillation conditions in a distillation system under vacuum distillation conditions and adding to said system a polymerization inhibitor consisting essentially of a mixture of N-nitroso diphenyl amine and a dinitro-o-cresol, wherein said mixture contains 10 to 90% by weight of N-nitroso diphenyl amine with the remainder being a dinitro-o-cresol and wherein said inhibitor is used in an amount of 50 to 3000 ppm by weight of said vinyl aromatic compound.

2. The process as defined by claim 1, wherein said vinyl aromatic compound is styrene.

3. The process as defined by claim 1, wherein said vinyl aromatic compound is alpha-methyl styrene.

4. The process as defined by claim 1, wherein said polymerization inhibitor is added continuously to said distillation system.

5. The process as defined by claim 1, wherein the dinitro-o-cresol is 4,6-dinitro-o-cresol.

6. The process as defined by claim 1, wherein said mixture contains 40% to 60% by weight of N-nitroso diphenyl amine with the remainder being a dinitro-o-cresol.

7. The process as defined by claim 2 wherein said inhibitor is used in an amount of 100 to 600 ppm by weight of said styrene.

8. The process as defined by claim 2 wherein said inhibitor is used in an amount of 200 to 600 ppm by weight of said styrene.

9. The process as defined by claim 1, wherein the dinitro-o-cresol is 3,5-dinitro-o-cresol.

10. The process as defined by claim 1, wherein said vacuum distillation conditions comprise a reboiler temperature of between about 150° and 250° F. and a reboiler pressure of from about 30 mm to about 400 mm of Hq.

11. The process as defined by claim 2, wherein the combined inhibitor is used in an amount of 400 ppm by weight of said styrene.

12. The process as defined by claim 2, wherein the combined inhibitor is used in an amount of 200 ppm by weight of said styrene.

* * * * *